United States Patent
Ladebeck et al.

(10) Patent No.: US 8,073,525 B2
(45) Date of Patent: Dec. 6, 2011

(54) COMBINED PET/MRT UNIT AND METHOD FOR SIMULTANEOUSLY RECORDING PET IMAGES AND MR IMAGES

(75) Inventors: Ralf Ladebeck, Erlangen (DE); Wolfgang Renz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1505 days.

(21) Appl. No.: 11/508,179

(22) Filed: Aug. 23, 2006

(65) Prior Publication Data

US 2007/0055127 A1    Mar. 8, 2007

(30) Foreign Application Priority Data

Aug. 24, 2005    (DE) .......................... 10 2005 040 107

(51) Int. Cl.
*A61B 5/05* (2006.01)
(52) U.S. Cl. ........................................ 600/411; 600/407
(58) Field of Classification Search .................. 600/436, 600/407, 411
See application file for complete search history.

(56) References Cited

U.S. PATENT DOCUMENTS

| | | | |
|---|---|---|---|
| 4,939,464 A | 7/1990 | Hammer | |
| 7,835,782 B2 * | 11/2010 | Cherry et al. | 600/411 |
| 2003/0090267 A1 | 5/2003 | Rubashov | |
| 2006/0250133 A1 | 11/2006 | Krieg et al. | |

FOREIGN PATENT DOCUMENTS

| | | |
|---|---|---|
| DE | 10 2005 015 071 | 10/2006 |
| WO | WO 03/003038 | 1/2003 |

OTHER PUBLICATIONS

German Office Action dated Jun. 27, 2006 for counterpart German Patent Application No. 10 2005 040 107.4-35.
PET camera CTI-951R-31 (ECAT 951).

* cited by examiner

*Primary Examiner* — Tse Chen
*Assistant Examiner* — Elmer Chao
(74) *Attorney, Agent, or Firm* — Harness, Dickey & Pierce, P.L.C.

(57) ABSTRACT

A combined PET/MRT unit is disclosed that includes a PET detector which is reduced by comparison with the prior art, and that consists, for example, of a PET detector with a polygonal arrangement of the detector elements or with a PET detector ring. The PET detector is reduced in an axial direction by comparison with the detectors of the prior art, as a result of which the costs for producing the expensive PET detectors are lowered. The reduction of the PET detector is possible because the MR measurement usually lasts longer than the PET measurement, and so a reduced PET detector can be used for the temporally sequential recording of a number of PET tomograms by mechanical displacement of the PET detector. Since the MR measurement lasts substantially longer, this mechanical displacement does not lead to a lengthening of the measuring time. The invention also relates to methods for simultaneously recording MR and PET tomograms in which the PET/MRT units according to the invention are used.

25 Claims, 2 Drawing Sheets

COMBINED PET/MRT UNIT AND METHOD FOR SIMULTANEOUSLY RECORDING PET IMAGES AND MR IMAGES

PRIORITY STATEMENT

The present application hereby claims priority under 35 U.S.C. §119 on German patent application number DE 10 2005 040 107.4 filed Aug. 24, 2005, the entire contents of which is hereby incorporated herein by reference.

FIELD

The present invention generally relates to a combined positron emission tomography/magnetic resonance tomography unit (PET/MRT unit) and/or an imaging method for simultaneously recording MR tomograms and PE tomograms, in the case of which method this PET/MRT unit may be used, for example. An example embodiment of the PET scanner contained in the PE tomograph of the combined PET/MRT unit makes it possible to reduce the costs of producing the PET/MRT unit according to an embodiment of the invention.

BACKGROUND

Magnetic resonance tomography (MRT) is an imaging method that enables tomograms of living organisms such as humans to be produced with high resolution. The patient is supported in a homogeneous magnetic field $B_0$. Gradient cores are used to modify the external magnetic field in the FOV (field of view) such that, firstly, a body slice is selected and, secondly, a spatial coding of the generated MR signals is performed.

During the subsequent reconstruction of the MR signals, for example by way of Fourier transformation, an image of the selected slice is produced that is used for medical diagnostics. Generation and detection of the MR signals are performed with the aid of a high-frequency system that includes a transmitting antenna, which irradiates HF excitation pulses into the patient, and a receiving antenna that detects the emitted HF resonance signals and relays them for the purpose of image reconstruction. Depending on the diagnostic task, the contrast of the MR images can be diversely varied by selecting a suitable pulse sequence, such as a spine echo sequence or a gradient echo sequence, and the sequence parameters associated therewith. The MRT images body structures and consequently constitutes a structural imaging method.

Another method for producing tomograms of a patient is positron emission tomography (PET). This nuclear medicine method is used to display the distribution of a radioactively marked substance in the organism. The substance is introduced into the organism and becomes concentrated in specific body tissues in accordance with its biochemical function. The subsequent decay of the radionuclide in this substance in conjunction with positron emission is detected and measured data are supplied that can be reconstructed to form a tomogram that images chiefly biochemical, that is to say physiological, processes.

PET is thus a method for functional imaging. Since the abovementioned processes take place chiefly in specific body compartments such as organs, PET also supplies structural information, but with a substantially lesser resolution than MRT.

Radiopharmaca with radionuclides contained therein which emit positrons upon decay ($\beta^+$ decay) are suitable for PET. After a short distance of approximately 1 mm, a positron interacts with an electron. In this process, the two particles are annihilated with the production of two photons in the region of gamma radiation, and these move away from one another on a line, that is to say at an angle of 180°.

Use is made for the purpose of detecting the two photons of a PET detector that is also denoted as a PET camera or PET scanner and which surrounds the measurement object. The PET detector includes a large number of detector elements that are arranged about the measurement object, which is to be imaged.

There are various configurations for the arrangement of the detector elements. Most frequently, the detector elements are arranged on a ring that surrounds the measurement object and is completely occupied with detector elements. Such a PET scanner is also denoted as a stationary block ring system.

However, it is also possible to use a smaller number of large-area position sensitive detector elements in a polygonal arrangement. Moreover, it is possible to use a ring that is occupied only partially with detector elements, there being a need in this case for the ring, and thus the detector elements, to be rotated about the measurement object in order to acquire the requisite measured data. Such a system is also denoted as a rotating block ring system. According to a further general refinement, the PET scanner comprises curved continuous panels.

The directions in a detector ring are usually specified as follows: the direction from the center of the detector ring to the circular circumference on which the detector elements are fastened is the radial direction. The direction along the circular circumference is denoted as the transaxial direction. The axis on which the patient couch is arranged is the axial direction, which is also denoted as z-axis in the attached figures.

In order to improve the total detection efficiency, in modern PET scanners the PET detector usually has a length of at least 15 cm in an axial direction. This can be achieved by stacking a number of detector rings directly one after another, or by using two-dimensionally continuous detectors of large axial dimension and having the length specified above. In the case of a number of detector rings, the total number of the detector elements is typically of an order of magnitude of approximately 10 000.

In the basic design, the detector elements situated exactly opposite one another are firstly connected in a state of electronic coincidence, that is to say they register an event only when a photon originating from a positron decay is respectively registered during a very short interval (3-10 ns) at these two detector elements. Such a design would, however, enable the registration only of photons that originate from a radionuclide that is localized exactly at the center of the relevant detector ring inside the measurement object. In order to detect the decay of radionuclides with localization outside the center, that is to say for pictorially acquiring an extended measurement object, each detector element must be connected in a state of electronic coincidence to a fan of detector elements that are situated opposite this detector element on the detector ring. This arrangement, which is also denoted as computed tomography, is illustrated schematically in FIG. 1.

The PET camera CTI-951R-31 (Knoxville, Tenn., USA) from Siemens is specified as an example of a PET detector ring system. This PET scanner includes 16 detector rings following one after another in an axial direction and in each case having a diameter of 102 cm. 512 BGO (bismuth germanium oxide) crystals sensitive to γ quanta are arranged on each detector ring in a fashion corresponding to a total number of detector elements of 8192 BGO crystals for all the detector rings. Each detector element (BGO crystal) has a size of 6.25 mm (transaxial)×6.75 mm (axial)×30 mm (radial).

The PET scanner can, for example, also include four or six flat detectors. The X ring/4R PET camera (Nucline™), which includes four separate rectangular detectors made from NaI (TI) crystals with a size of 260 mm×246 mm in each case is given as an example of such a PET scanner. This camera is normally used for examining small objects.

In order to carry out the PET method, the radiopharmacon is injected in the patient or administered by inhalation. The patient is positioned on a moveable table such that the body section to be examined is situated in the target region of the detectors. A complete PET scan includes the detection of a large number of photon pairs that is typically in the range from $10^6$ to $10^8$. The subsequent image reconstruction converts the signals thus detected into a 2D image, and this reproduces in a quantitative way the distribution of the radiopharmacon in the measurement object.

As a structural imaging method and a functional imaging method, respectively, MRT and PET supply different information. It is therefore sensible to combine the image information of the two methods, something which enables particularly precisely determined anatomical structures to be assigned to regions with a high concentration of the radiopharmacon, such as organs or cancerous ulcers. The relatively low spatial resolution of PET can be overcome in this way. For future systems, an attempt is therefore currently being made to combine the imaging methods of MRT and PET in one unit, and to render them capable of use as simultaneously as possible.

It is pointed out in this context that combinations of a PET scanner and a computer tomography are already commercially available. For the purpose of examination in such a combined PET/CT unit, the patient is moved on the patient couch directly one after another through the detectors of the two components. Subsequently, the images produced are superimposed in the computer, thus combining the high spatial resolution of a CT with the functional information from PET.

Combined PET/MRT units are already currently under development. Here, an APD photodiode array with an upstream array composed of LSO crystals finds favor as PET detector.

It is to be considered when developing combined PET/MRT units that PET is one of the most expensive imaging methods in medicine. A not insubstantial contribution to the high costs is made by the costly PET detector. Consequently, cost effective approaches to the configuration of the PET detector are advantageous for mass production with reference to a commercial PET/MRT unit.

A combined PET/MRT unit is described in US patent application US 2003/0090267 A1.

SUMMARY

A combined PET/MRT unit is disclosed, in at least one embodiment, that can be produced in a more cost effective manner by way of a suitable design of the PET detector. Furthermore, in at least one embodiment, a combined PET/MRT imaging method is disclosed in which this combined PET/MRT unit is used.

In at least one embodiment, a combined positron emission tomography magnetic resonance tomography unit (PET/MRT unit) comprises:
a magnetic resonance tomography that has at least one basic field magnet, a system of gradient coils, a high-frequency system, which comprises an MR antenna, for generating HF excitation pulses and for detecting the emitted resonance signals, a couch on which the measurement object can be moved into the MR tomography in an axial direction (z-axis), a PET detector that has at least two detector elements for detecting the gamma radiation emitted from the measurement object, the detector elements being arranged about the measurement object on a circular periphery and having at least a size such that the gamma radiation formed on the line between the detector elements in the measurement object and emitted in the direction of the detector elements is detected, and
one or more unit computers including control software for processing the resonance signals, detected by the MR antenna, and the gamma radiation, detected by the PET detector, for storing the MRT data and the PET data and for displaying the MR images and the PET images.

The inventive PET/MRT unit of at least one embodiment includes a PET detector that can be displaced in an axial direction and has in the axial direction a lesser extent than the MR antenna, which is selected such that the PET detector must be displaced in an axial direction in order to detect the same number of layers or cross-sectional surfaces of the measurement object as the MR antenna.

The measurement object can, for example, be a human or an animal.

A basic arrangement for the combination of the detector of the MR tomography and the PET detector is described in the German patent application from Siemens having the official file reference 10 2005 015 071.3, the entire contents of which are hereby incorporated herein by reference.

The at least two detector elements forming the PET detector must be so large that the requirements placed on the point pattern function are fulfilled, that is to say that the gamma radiation emitted by the two detector elements on the line between the two detector elements, the so called line response (LOV), in a direction of these elements is reliably detected by the two detector elements in the case of coincidence.

When the PET detector includes exactly two detector elements, at least one of these two detector elements must be rotated about the measurement object over a certain angular range so that all the measured data required for reconstructing the PET image of a slice of the measurement object can be acquired. Such a PET detector is possible in principle, but is of only relatively low efficiency, since the measuring time is very much lengthened because of the small detector area and the required far-reaching rotation of an element.

The advantage of the inventive combined PET/MRT unit of at least one embodiment resides in the fact that the PET detector included therein can be reduced very substantially in an axial direction, and that the costs of the combined unit can thereby be lowered. Because of the reduced size in an axial direction, it is certainly possible to measure only fewer layers with this smaller PET detector than with a normal known PET detector, but since the MR examination generally lasts substantially longer than the acquisition of PET data, further PET tomograms of the measurement object can be recorded by displacing the PET detector during the period for detecting all the MR signals with the MR antenna.

According to an example inventive embodiment of the combined PET/MRT unit, the extent of the PET detector in an axial direction is such that the measured data for the PET images from at most 1 to 5, and preferably at most 1 to 3 layers, can be acquired without displacing the PET detector. Most preferably, the measured data from exactly one layer of the measurement object (5) can be acquired with the PET detector.

The PET detector can be of different configurations. It can particularly preferably be selected from among the following embodiments, which are illustrated in FIG. 1:

the PET detectors that include two separate large-area detector plates that are arranged parallel to one another on opposite sides of the measurement object and that can be rotated (FIG. 1a) or cannot be rotated (FIG. 1b) in a transaxial direction about the measurement object for the purpose of complete data acquisition, the PET detectors that include a number of large-area detector plates that surround (FIG. 1c)) the measurement object completely in a polygonal arrangement, the number of the detector plates being even and comprising 4, 6, 8, 10, 12, 14, 16 . . . etc. plates. Such PET detectors are usually denoted as continuous detector panels. Likewise, the number of the detector plates can be odd.

the PET detectors that include a detector ring that surrounds the measurement object and is completely occupied with small PET detector elements, (FIG. 1d)), and the PET detectors that include a detector ring that is partially occupied with small detector elements whose number and distribution on the detector ring are selected such that the acquisition of all the measured data that are required for producing the PET images of one or more layers of the measurement object is possible with or without rotation of the detector ring (FIG. 1f)).

The PET detector is very particularly preferred to be a PET detector ring that is completely occupied with small detector elements.

In the case of a PET detector ring that is occupied only partly with detector elements and requires a rotation, the detector ring is firstly rotated about the measurement object until all the measured data for a first complete PET image of the relevant slice have been acquired. Subsequently, the PET detector is displaced in an axial direction, that is to say in the direction in which the patient is supported, that runs perpendicular to the circular circumference on which the detector elements are arranged. After a displacement of the detector ring as far as the next slice of the measurement object, the next PET image can be recorded by rotating the PET detector ring. A number of MR tomograms are continuously acquired with the stationary MR antenna during these various displacement and rotation steps, and so no overall lengthening of the measuring time comes about.

According to a further example inventive embodiment, a number of these PET detectors can be stacked directly one after another in an axial direction with the proviso that the extent of the resulting PET detector is less in an axial direction than the extent of the MR antenna. It is possible in this way for a number of slices to be detected simultaneously with the PET detector, although the PET detector then becomes somewhat more expensive.

The MR antenna is preferably arranged inside the PET detector and is separated therefrom for the purpose of mutual decoupling of interference by a PET transparent and MR compatible HF shield.

According to an example embodiment of the invention, the MR antenna can also be installed such that it can move in an axial direction, the MR antenna and the PET detector then having a common drive unit or separate drive units, both the common drive unit and the separate drive units enabling the independent movement of the MR antenna and the PET detector in an axial direction.

The displacement of the PET detector in an axial direction, and the rotation, required if appropriate, about the measurement object are preferably performed according to an example embodiment of the invention with the aid of an MR compatible drive unit. An MR compatible drive unit is understood as a drive unit whose components and whose electronics that may be present interfere neither with the homogeneous magnetic field nor with the signal detection.

The drive unit of the PET detector can be arranged inside the magnet and includes a fluid hydraulics or a compressed air hydraulics. However, it can also be arranged outside the magnet, in which case the drive is then transmitted with the aid of Bowden cables, push rods or toothed belts. Only the PET detector is moved in this case.

Alternatively, the PET detector can be permanently connected to the patient couch, the drive unit of the PET detector then consisting of the drive unit of the patient couch. In this case, the PET detector can be displaced in an axial direction together with the patient couch.

The drive unit of the MR antenna can include the drive unit of the patient couch. The MR antenna can then be displaced in an axial direction together with the patient couch, it then being possible to design the PET detector in a stationary fashion. It is possible with the aid of this embodiment to carry out combined MRT/PET measurements during which the MRT measurement is terminated before the PET measurement, thereby rendering it necessary to displace the position of the MR antenna in order to detect another MR stage.

The PET detector of at least one embodiment of the inventive combined PET/MRT unit can have the arrangement of detector elements that has been specified further above, the detection of the annihilation radiation requiring at least two detector elements opposite one another and of which one can be moved on a circular circumference about the measurement object. Such a system is, however, not particularly effective, and so the PET detector usually includes a small number of large-area, position-sensitive detectors in a polygonal arrangement, or a large number of detector elements, for example block detectors, that are arranged about the object to be imaged. In the latter case, in a transaxial direction and/or axial direction the detector elements have a length that is in the range from 0.5 to 10 cm, preferably 0.5 to 7.5 and, more preferably, 0.5 to 5 cm.

By way of example, it is possible here to specify the PET detector ring system, already mentioned above, of the PET camera CTI-951R-31, that comprises 16 detector rings. According to at least one embodiment of the invention, use may be made by way of example of only one detector ring in the combined MRT/PET unit, such as is used in this PET camera as part of the ring array. In this case, each of the 512 detector elements on this detector ring has a transaxial extent of 6.25 mm, an axial extent of 6.75 mm and a radial extent of 30 mm. In very general terms, the individual detector elements can have a transaxial and an axial extent such that the requirements placed on the point image function are in fact still fulfilled, that is to say the signals continue to be detected with a sensitivity such that the PET image of a slice can be produced.

The PET detector of the inventive MRT/PET unit preferably includes a photodiode array and an upstream array made from a detector material that is sensitive to gamma radiation and is, for example, selected from among lutetium oxyorthosilicate (LSO), cerium doped LSO, cerium doped lutetium yttrium aluminum perovskite, bismuth germanium oxide (BGO), sodium iodide (NaI) and thallium doped NaI. The photodiode array that is combined with detector elements sensitive to gamma radiation is advantageously an APD photodiode array. The PET detector of the inventive combined PET/MRT unit preferably consists of an array of APD/LSO detectors that extends in an axial direction and in a circumferential direction about the patient.

APD photodiodes are based on PIN photodiodes that include a p-doped and an n-doped semiconductor layer that are separated from one another by an intrinsic undoped layer. In the case of APN photodiodes, an applied high electric field in the intrinsic zone amplifies the electron current by electronic ionization in the carrier material (avalanche effect). LSO crystals have a particularly high sensitivity to the photons occurring and, as a constituent of the PET detector, therefore supply a clearer, more informative image.

The subject matter of at least one embodiment of the present invention also includes various imaging methods that enable the simultaneous recording of PET pictures and MR pictures.

In accordance with an example embodiment, the invention relates to a combined PET/MRT imaging method for simultaneously recording one or more MRT tomograms and one or more PET tomograms that comprises the following steps:

introducing a measurement object into a combined PET/MRT unit, recording the MR tomograms by carrying out the method steps customary in MR tomography, recording the PET tomograms by carrying out the steps customary in PE tomography;

this method is characterized in that it is carried out with the aid of one of the inventive combined PET/MRT units described further above.

According to an example embodiment of the inventive method, the PET images are recorded sequentially by mechanically displacing the PET detector in an axial direction and, if appropriate, rotating the PET detector in a peripheral direction about the measurement object, and the MR images are recorded while maintaining the position of the MR antenna, the position of the patient couch and the position of the measurement object. The rotation is required whenever the measurement object is surrounded by so low a number of detector elements that without such a rotation it is possible to acquire only the PET signals of a part of the measurement object. The rotation of the PET detector can be dispensed with if the measurement object is completely surrounded in a plane by PET detector elements.

According to a further example embodiment of the inventive method, the PET image(s) is/are recorded in conjunction with parallel mechanical displacement of the patient couch and of the PET detector, permanently connected to the patient couch, in an axial direction and, if appropriate, rotation of the PET detector in a peripheral direction about the measurement object, and a number of MR images are sequentially recorded while maintaining the position of the MR antenna, the measuring range for the MR images then being greater in an axial direction than the extent of the MR antenna in this direction. This method can be applied when the MR measurement is terminated before the PET measurement.

Alternatively, the abovedescribed sequential recording of MR images by mechanical displacement of the MR antenna can be performed in an axial direction. In the case of this embodiment, the PET images are recorded while maintaining the position of the PET detector that is, if appropriate, additionally rotated in a circumferential direction about the measurement object, and while maintaining the position of the patient couch and of the measurement object.

It is particularly preferred for the possibility of selecting between the abovedescribed three embodiments when the PET detector and the MR antenna can be moved simultaneously and independently of one another.

The recording of the MR image(s) usually comprises the following steps:

positioning the region of interest of the measurement object in the basic magnet, carrying out a pulse sequence in the presence of a homogeneous magnetic field $B_0$ that includes irradiating HF excitation pulses, which are emitted by the MR antenna of the HF system, switching gradient fields for the purpose of slice selection and spatial coding with the aid of gradient coils, and detecting the emitted resonance signals with a receiving antenna of the HF system, relaying to the unit computer the MR resonance signals registered and processed by the HF system, and producing the MR tomograms and displaying the MR tomograms with the aid of a unit computer.

The abovementioned steps can be supplemented by all method steps that are normally applied when carrying out MR imaging methods as known in the prior art.

The recording of the PET image(s) comprises, inter alia, the following steps:

positioning the region of interest of the measurement object in the PET detector that surrounds the measurement object, introducing a radiopharmacon into the measurement object by injection or inhalation, detecting with the PET detector the photons emitted by the measurement object as a consequence of the positron decay, and reconstructing the PET tomograms with the aid of the detected PET signals in the unit computer.

The pulse sequence can be one of the normal spine echo sequences or gradient echo sequences, or one of the known mixed forms of an SE sequence and a GE sequence, that is to say the embodiments of the inventive method can be carried out for all known MR pulse sequences.

BRIEF DESCRIPTION OF THE DRAWINGS

The inventive MRT/PET unit is described below with the aid of example embodiments with reference to the attached figures, of which.

DETAILED DESCRIPTION OF THE EXAMPLE EMBODIMENTS

Figure 1A:
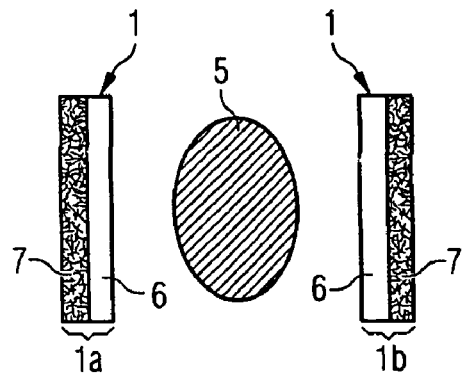
FIGS. 1a)-1e) show embodiments of the PET detector that can be used in accordance with the invention.

FIG. 1 shows the PET detectors in radial and transaxial directions. The axial direction, that is to say the direction in which the measurement object is supported on a couch, which corresponds to the direction in which the size of the PET detector is reduced, according to an embodiment of the invention, to a value that is as small as possible in order to be able to produce cost effective PET detectors therefore runs perpendicular to the plane of the paper. FIG. 1 illustrates various PET detector arrangements that can be used according to an embodiment of the invention. In accordance with FIG. 1a), the PET detector 1 consists of two large-area position-sensitive detector plates 1a, 1b, between which the measurement object 5 is inserted. As in all the example embodiments in accordance with FIG. 1, these detector plates 1a, 1b comprise a crystalline layer 6 that is sensitive to gamma radiation, and a layer, arranged therebehind, composed of photomultipliers 7. In FIG. 1a), the detector plates 1a, 1b have axial and transaxial extents such that a rotation of the detector plates 1a, 1b about the measurement object 5 is not required.

Figure 1B:
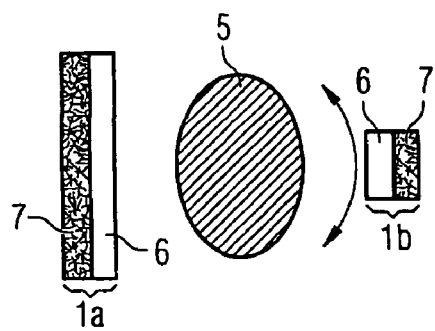
Figure 1C:
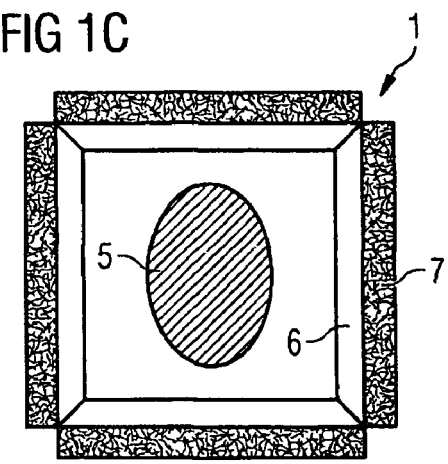

In the case of the embodiment in accordance with FIG. 1b), the PET detector has so few detector elements 1a, 1b that it must be rotated about the measurement object 5 in the direction of the arrow in order to acquire the data completely. FIG. 1c) shows two PET detectors 1 of polygonal shape that surround the measurement object 5 completely. The illustrated PET detectors 1 consist of four to six detector elements 1a, 1b. A rotation of the PET detector 1 is not required.

Figure 1D:
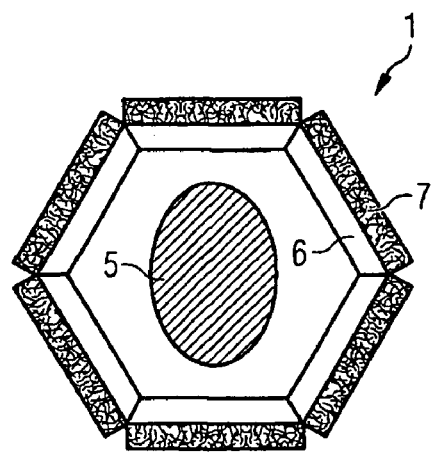
Figure 1D:
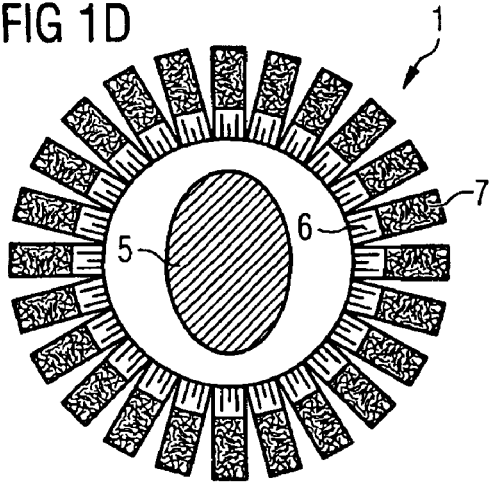
Figure 1E:
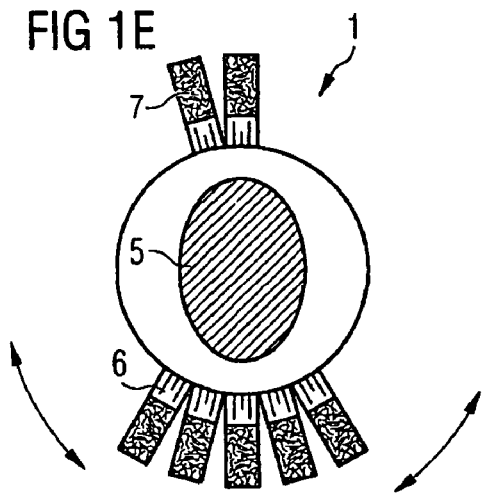

For a very large number of detector elements, the polygon merges into the detector ring shown in FIG. 1d). This detector ring 1 is completely occupied with detector elements, and so a rotation of the ring is not required when measuring in the circumferential direction about the measurement object. In accordance with FIG. 1e), the PET detector ring has a substantially smaller number of detector elements such that, if appropriate, a rotation of the detector ring 1 about the measurement object 5 is required.

Figure 2:
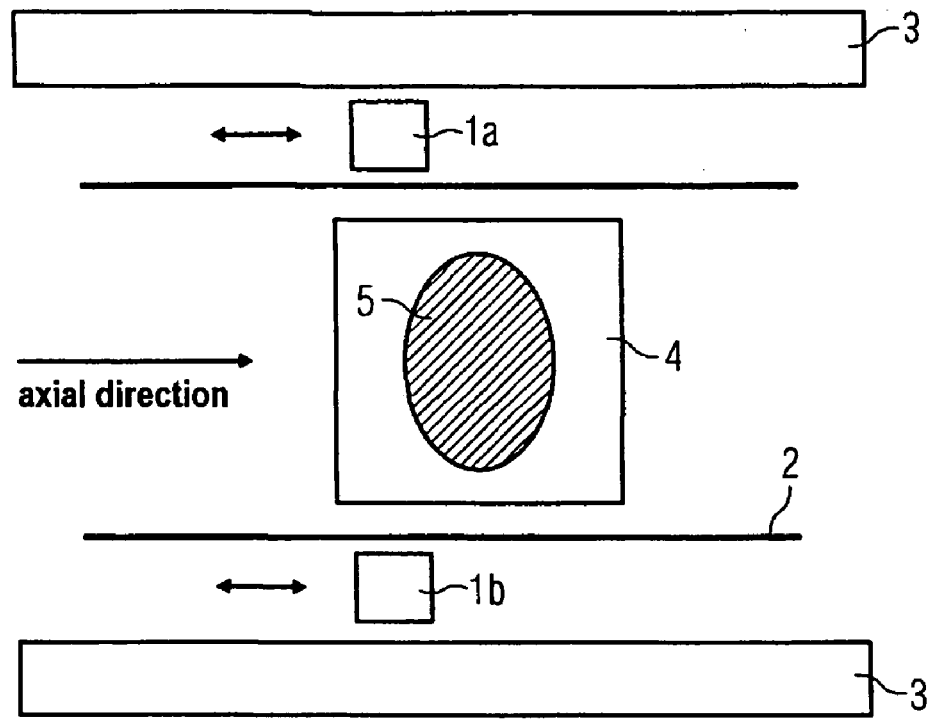
FIG. 2 is a schematic of an MRT/PET unit that is used in the case in which the PET imaging is performed more quickly than the MR imaging.

FIG. 2 shows an inventive MRT/PET unit in a schematic cross sectional view that includes the axial direction in which the PET detector 1 and the patient couch can be displaced. The PET detector ring 1, indicated by two detector elements 1a and 1b, is arranged inside the gradient coil 3 and outside the MR antenna 4 of the MR tomography, there being inserted between the PET detector ring 1 and the MR antenna 4 an HF shield 2 that ensures the mutual decoupling of interference between the MR antenna 4 and the PET detector 1. The PET detector ring 1 and the MR antenna 4 have a diameter such that a patient can be introduced into the ring on a patient couch and supported.

The PET detector ring 1 can be moved in an axial direction, something which is indicated by the two double arrows to the left of the detector elements 1a, 1b. The substantially wider MR antenna 4 (=greater extent in an axial direction) is not moved. Within the period in which the complete data are acquired for reconstructing many MR tomograms without displacing the MR antenna 4 and the measurement object 5, the data for an equally large number of PET tomograms are acquired sequentially in time by displacing the narrow PET detector ring in an axial direction in stepwise fashion. The mechanical drive of the PET detector ring must be MR compatible, so that no disturbance is caused to the MR examination running in parallel. The PET detector includes an APD photodiode array with an upstream array composed of LSO crystals.

Since the MR measurement lasts substantially longer than the PET data acquisition, the narrow PET detector ring can be used for the PET data acquisition without increasing the total measuring time thereby. Because of the narrow design of the PET detector ring, a cost reduction is achieved for a series production of a combined PET/MRT unit.

FIG. 2 also corresponds to the case in which instead of a complete PET detector ring 1 use is made of only two PET detector elements 1a, 1b that, as illustrated in FIG. 2, are arranged opposite one another. When use is made of two PET detector elements 1, at least one of the two elements 1a, 1b must be moved around a circular circumference around the MR antenna 4 in order to acquire all the measured data for a slice before the two detector elements 1a, 1b are displaced in the z direction in order to record further measured data in another slice. In the case of only two detector elements 1, the measuring time is correspondingly lengthened such that the efficiency of the measurement declines. At the same time, however, this also enables a further cost reduction on the basis of the once again reduced surface of the two PET detector elements 1.

Figure 3:
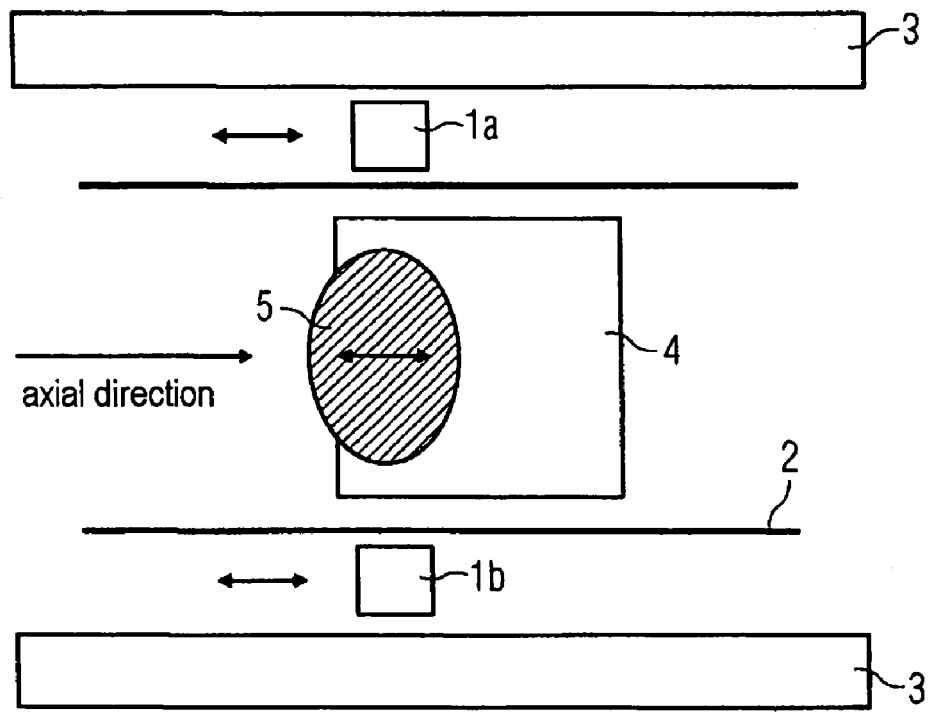
FIG. 3 is a schematic of an MRT/PET unit that is used in the case in which the MR imaging is performed more quickly than the PET imaging.

FIG. 3 shows a PET/MRT unit according to an embodiment of the invention in the case of which the PET detector ring 1 is permanently connected to the patient couch such that the measurement object 5 and the PET detector ring 1 can be displaced in parallel, while the MR antenna 4 is stationary in the usual way. This arrangement is used when the MR data acquisition is performed more quickly than the acquisition of the PET measured values. Firstly, a start is made in acquiring the PET measured data and the MR measure data without the MR antenna 4 or the PET detector 1 being displaced. At a specific instant, the MR data acquisition is terminated, while the acquisition of the PET measured data continues. At this instant, the patient couch together with the patient and PET detector ring 1 is displaced, while the MR antenna remains unchanged, something which permits another MR stage to be detected.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A combined positron emission tomography/magnetic resonance tomography (PET/MRT) unit, comprising:
 a magnetic resonance (MR) tomography unit including at least one basic field magnet, a system of gradient coils, and a high-frequency (HF) system, including an MR antenna, to generate HF excitation pulses and to detect emitted resonance signals, a measurement object being movable into the MR tomography unit in an axial direction;

a PET detector including at least two detector elements to detect gamma radiation emitted from the measurement object, the at least two detector elements being arranged about the measurement object at a circular periphery and having at least a size such that gamma radiation formed on a line between the at least two detector elements in the measurement object and emitted in the direction of the at least two detector elements is detected; and at least one unit computer, including control software to process the emitted resonance signals detected by the MR antenna, and the gamma radiation detected by the PET detector, to store MRT data and PET data and to display MR images and PET images; wherein the PET detector is displaceable in the axial direction and is narrower than the MR antenna in the axial direction, a width of the PET detector in the axial direction is selected such that the PET detector must be displaced in the axial direction in order to detect a same number of at least one of layers and cross-sectional surfaces of the measurement object as the MR antenna, the MR antenna is installed to be movable in the axial direction, and the MR antenna and the PET detector include at least one of a common drive unit and separate drive units, enabling independent movement of the MR antenna and the PET detector in the axial direction.

2. The combined PET/MRT unit as claimed in claim 1, wherein the width of the PET detector in the axial direction is such that measured data for the PET images from at most 5 layers of the measurement object are acquirable without displacing the PET detector.

3. The combined PET/MRT unit as claimed in claim 1, wherein the PET detector includes at least one of:

a PET detector that includes two separate large-area detector plates, arranged parallel to one another on opposite sides of the measurement object and rotatable in a transaxial direction about the measurement object for the purpose of complete data acquisition;

a PET detector that includes a number of large-area detector plates that surround the measurement object in a polygonal arrangement, the number of the detector plates being at least one of even and odd;

a PET detector that includes a detector ring that surrounds the measurement object and is completely occupied with PET detector elements; and a PET detector that includes a detector ring that is partially occupied with PET detector elements whose number and distribution on the detector ring are selected such that acquisition of all measured data required for producing the PET images of at least one layer of the measurement object is possible with or without rotation of the detector ring.

4. The combined PET/MRT unit as claimed in claim 3, wherein a number of PET detectors are stacked directly one after another in the axial direction to form a resulting PET detector, a width of the resulting PET detector in the axial direction being less than a width of the MR antenna in the axial direction.

5. The combined PET/MRT unit as claimed in claim 1, wherein the MR antenna is arranged inside the PET detector and is separated therefrom for the purpose of mutual decoupling of interference by a PET transparent and MR compatible HF shield.

6. The combined PET/MRT unit as claimed in claim 1, wherein a drive unit of the PET detector is at least one of arranged inside the at least one basic field magnet and includes at least one of fluid hydraulics and compressed air hydraulics, and arranged outside the at least one basic field magnet, the transmission of the drive being performed with the aid of at least one of Bowden cables, push rods and toothed belts.

7. The combined PET/MRT unit as claimed in claim 1, wherein the PET detector is permanently connected to a patient couch, and wherein a drive unit of the PET detector includes a drive unit of the patient couch such that the PET detector is displaceable in the axial direction together with the patient couch.

8. The combined PET/MRT unit as claimed in claim 1, wherein a drive unit of the MR antenna includes a drive unit of the patient couch such that the MR antenna is displaceable in the axial direction together with the patient couch.

9. The combined PET/MRT unit as claimed in claim 1, wherein, in at least one of a transaxial direction and the axial direction, the at least two detector elements of the PET detector have a length that is in the range from 0.5 to 10 cm.

10. The combined PET/MRT unit as claimed in claim 1, wherein the PET detector includes a photodiode array and an upstream array made from a detector material that is sensitive to gamma radiation and is selected from the group consisting of lutetium oxyorthosilicate (LSO), cerium doped LSO, cerium doped lutetium yttrium aluminum perovskite, bismuth germanium oxide (BGO), sodium iodide (NaI) and thallium doped NaI.

11. The combined PET/MRT unit as claimed in claim 10, wherein the photodiode array is an APD photodiode array.

12. A combined positron emission tomography/magnetic resonance tomography (PET/MRT) imaging method for simultaneously recording at least one MR tomogram and at least one PE tomogram, the method comprising:

introducing a measurement object into a combined PET/MRT unit;

recording the at least one MR tomogram by carrying out MR tomography; and recording the at least one PE tomogram by carrying out PE tomography, wherein the combined PET/MRT imaging method is carried out in a combined PET/MRT unit as claimed in claim 1.

13. The method as claimed in claim 12, wherein a plurality of PE tomograms are recorded sequentially by mechanically displacing the PET detector in the axial direction and wherein the at least one MR tomogram is recorded while maintaining the position of the MR antenna, the position of a patient couch and the position of the measurement object.

14. The method as claimed in claim 12, wherein the at least one PE tomogram is recorded in conjunction with parallel mechanical displacement of a patient couch and of the PET detector, permanently connected to the patient couch, in the axial direction and a number of MR tomograms are sequentially recorded while maintaining the position of the MR antenna, the measuring range for the number of MR tomograms being greater in the axial direction than a width of the MR antenna in the axial direction.

15. The method as claimed in claim 12, wherein a plurality of MR tomograms are recorded sequentially by mechanically displacing the MR antenna in the axial direction, and the at least one PE tomogram is recorded while maintaining the position of the PET detector and while maintaining the position of a patient couch and of the measurement object.

16. The method as claimed in claim 12, wherein the PET detector and the MR antenna are moved simultaneously and independently of one another.

17. The method as claimed in claim 12, wherein recording of the at least one MR tomogram comprises:
positioning a region of interest of the measurement object in the at least one basic field magnet;
carrying out a pulse sequence in the presence of a homogeneous magnetic field that includes irradiating HF excitation pulses emitted by the MR antenna of the HF system, switching gradient fields for the purpose of slice selection and spatial coding with the aid of gradient coils, and detecting the emitted resonance signals with a receiving antenna of the HF system;
relaying to the at least one unit computer the MR resonance signals registered and processed by the HF system; and
producing the at least one MR tomogram and displaying the at least one MR tomogram with the aid of the at least one unit computer.

18. The method as claimed in claim 12, wherein recording of the at least one PE tomogram comprises:
positioning a region of interest of the measurement object in the PET detector that surrounds the measurement object;
introducing a radiopharmacon into the measurement object by at least one of injection and inhalation;
detecting with the PET detector the photons emitted by the measurement object as a consequence of the positron decay; and
reconstructing the at least one PE tomogram with the aid of the detected PET signals in the at least one unit computer.

19. The combined PET/MRT unit as claimed in claim 1, wherein the width of the PET detector in the axial direction is such that the measured data for the PET images from exactly one layer of the measurement object is acquirable without displacing the PET detector.

20. The combined PET/MRT unit as claimed in claim 2, wherein the PET detector includes at least one of:
a PET detector that includes two separate large-area detector plates, arranged parallel to one another on opposite sides of the measurement object and rotatable in a transaxial direction about the measurement object for the purpose of complete data acquisition;
a PET detector that includes a number of large-area detector plates that surround the measurement object completely in a polygonal arrangement, the number of the detector plates being at least one of even and odd;
a PET detector that includes a detector ring that surrounds the measurement object and is completely occupied with PET detector elements; and
a PET detector that includes a detector ring that is partially occupied with PET detector elements whose number and distribution on the detector ring are selected such that acquisition of all measured data that are required for producing the PET images of at least one layer of the measurement object is possible with or without rotation of the detector ring.

21. The combined PET/MRT unit as claimed in claim 20, wherein a number of the PET detectors are stacked directly one after another in the axial direction to form a resulting PET detector, a width of the resulting PET detector being less than a width of the MR antenna in the axial direction.

22. The method as claimed in claim 17, wherein recording of the at least one PE tomogram comprises:
positioning the region of interest of the measurement object in the PET detector that surrounds the measurement object;
introducing a radiopharmacon into the measurement object by at least one of injection and inhalation;
detecting with the PET detector the photons emitted by the measurement object as a consequence of the positron decay; and
reconstructing the at least one PE tomogram with the aid of the detected PET signals in the at least one unit computer.

23. The method as claimed in claim 13, further comprising:
rotating the PET detector in a peripheral direction about the measurement object.

24. The method as claimed in 14, further comprising:
rotating the PET detector in a peripheral direction about the measurement object.

25. The method as claimed in claim 15, further comprising:
rotating the PET detector in a peripheral direction about the measurement object.

* * * * *